United States Patent
Alexander et al.

(10) Patent No.: US 12,325,686 B2
(45) Date of Patent: *Jun. 10, 2025

(54) METHODS AND SYSTEMS OF MONITORING FLAMMABILITY OF VARIOUS STREAMS DURING VINYL ACETATE PRODUCTION

(71) Applicant: Celanese International Corporation, Irving, TX (US)

(72) Inventors: Steve R. Alexander, Houston, TX (US); Kevin Clair Hanks, League City, TX (US); Stacey Somerville, Houston, TX (US); David S. C. Lee, Houston, TX (US); Christopher Paul Devlin, Corpus Christi, TX (US)

(73) Assignee: Celanese International Corporation, Irving, TX (US)

(*) Notice: Subject to any disclaimer, the term of this patent is extended or adjusted under 35 U.S.C. 154(b) by 117 days.

This patent is subject to a terminal disclaimer.

(21) Appl. No.: 18/330,696

(22) Filed: Jun. 7, 2023

(65) Prior Publication Data

US 2023/0312453 A1    Oct. 5, 2023

Related U.S. Application Data

(63) Continuation of application No. 17/772,459, filed as application No. PCT/US2020/070859 on Dec. 4, 2020, now Pat. No. 11,731,929.

(Continued)

(51) Int. Cl.
C07C 67/05       (2006.01)
B01J 19/00       (2006.01)
C07C 69/15       (2006.01)

(52) U.S. Cl.
CPC .......... *C07C 67/05* (2013.01); *B01J 19/0006* (2013.01); *C07C 69/15* (2013.01); *B01J 2208/00628* (2013.01)

(58) Field of Classification Search
CPC . C07C 67/05; C07C 69/15; B01J 2208/00628
See application file for complete search history.

(56) References Cited

U.S. PATENT DOCUMENTS 3,743,556 A    7/1973    Breton et al.
3,775,342 A    11/1973   Kronig et al.
(Continued)

FOREIGN PATENT DOCUMENTS

CN       1266051 A      9/2000
CN       104718182 B    8/2016
(Continued)

OTHER PUBLICATIONS

U.S. Appl. No. 17/772,459, Notice of Allowance, Mailed On Apr. 24, 2023, 8 pages.
(Continued)

*Primary Examiner* — Yate' K Cutliff
(74) *Attorney, Agent, or Firm* — Kilpatrick Townsend & Stockton LLP

(57) ABSTRACT

Methods and systems for producing vinyl acetate may use flammability limit (FL) formulas with improved efficiencies at more than one location in the vinyl acetate production process. Herein, FLs can be used at one or more of four portions of the vinyl acetate production process: the reactor, the process-to-process heat exchangers, the carbon dioxide removal system, and the ethylene recovery system. Such FLs are functions of operating conditions and include at least one interaction term that represents the interrelation of two or more of the operating conditions (e.g., temperature, pressure, and component concentration) on the FL.

20 Claims, 1 Drawing Sheet

Related U.S. Application Data

(60) Provisional application No. 62/950,264, filed on Dec. 19, 2019.

(56) References Cited

U.S. PATENT DOCUMENTS

| | | | |
|---|---|---|---|
| 5,557,014 | A | 9/1996 | Grate et al. |
| 5,990,344 | A | 11/1999 | Couves et al. |
| 5,998,659 | A | 12/1999 | Abel |
| 6,022,823 | A | 2/2000 | Augustine et al. |
| 6,057,260 | A | 5/2000 | Nicolau et al. |
| 6,410,817 | B1 | 6/2002 | Colling et al. |
| 6,472,556 | B2 | 10/2002 | Kitchen et al. |
| 8,993,796 | B2 | 3/2015 | Rinne et al. |
| 9,045,413 | B2 | 6/2015 | Aslam et al. |
| 9,573,877 | B2 | 2/2017 | Vismans et al. |
| 11,731,929 | B2 | 8/2023 | Alexander et al. |
| 2006/0167307 | A1 | 7/2006 | Saihata et al. |
| 2006/0247462 | A1 | 11/2006 | Saihata et al. |
| 2014/0066649 | A1 | 3/2014 | Vismans et al. |

FOREIGN PATENT DOCUMENTS

| | | | | |
|---|---|---|---|---|
| CN | 104736512 B | | 8/2017 | |
| EP | 0845453 A | * | 2/1998 | ........... C07C 67/055 |
| EP | 845453 A2 | | 6/1998 | |
| JP | 2000169430 A | | 6/2000 | |
| JP | 2008516906 A | | 5/2008 | |
| JP | 2018096943 A | | 6/2018 | |

OTHER PUBLICATIONS

Application No. CN202080087055.4, Notice of Decision to Grant, Mailed On Nov. 21, 2023, 2 pages.

Application No. PCT/US2021/039067, International Search Report and Written Opinion, Mailed On Oct. 26, 2021, 10 pages.

Application No. TW109141102, Office Action, Mailed On Jan. 17, 2024, 5 pages.

The Written Opinion and International Search Report of corresponding PCT application No. PCT/US2020/070859 mailed Mar. 10, 2021.

Notification of the First Office Action for CN Appln. No. 202080087055.4 dated Jun. 25, 2023, 4 pages.

Application No. JP2022-532573, Office Action, Mailed On Aug. 28, 2024, 3 pages.

Application No. EP20828237.6, Office Action, Mailed On Nov. 8, 2024, 5 pages.

Application No. TW109141102, Notice of Decision to Grant, Mailed On Sep. 18, 2024, 2 pages.

* cited by examiner

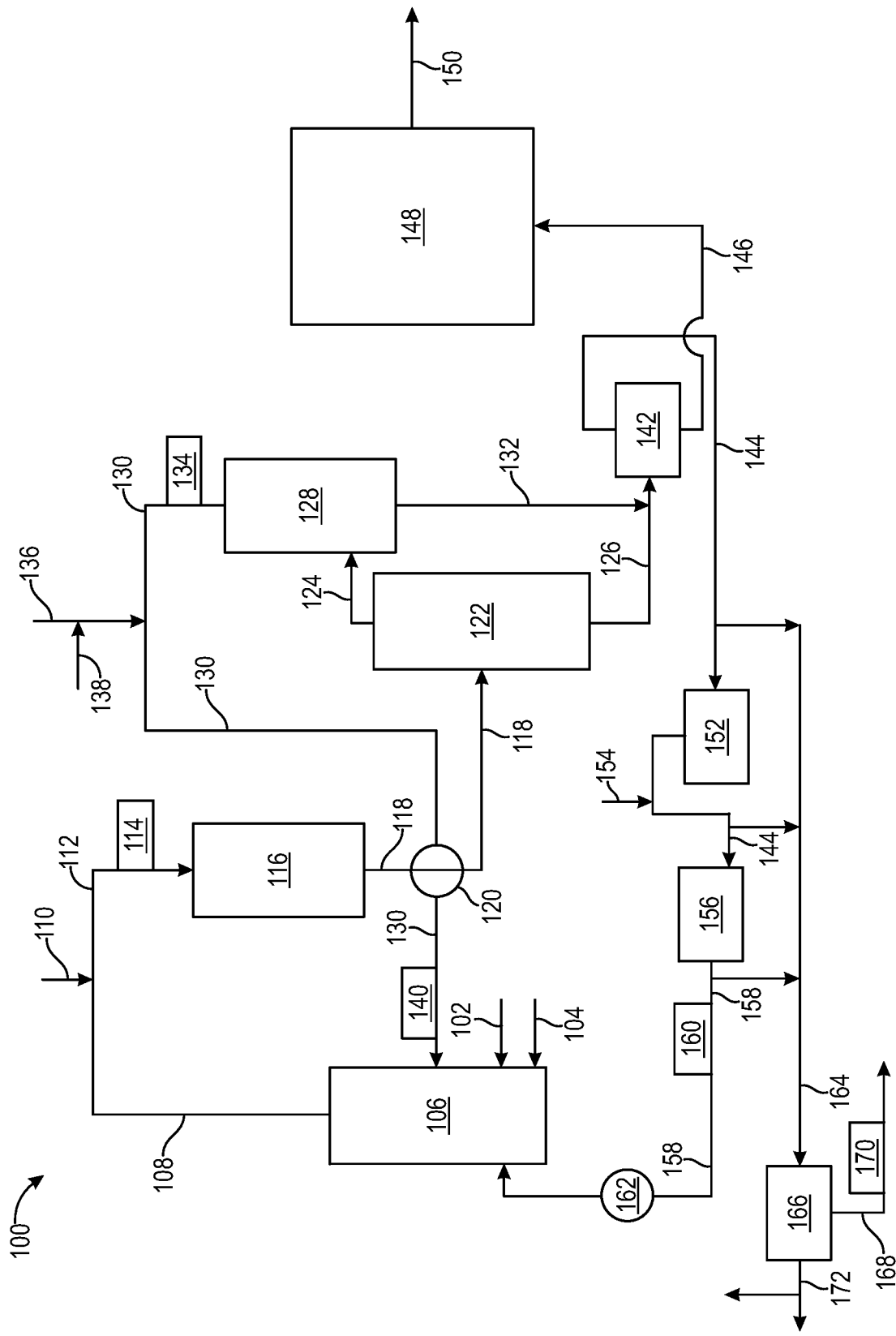

METHODS AND SYSTEMS OF MONITORING FLAMMABILITY OF VARIOUS STREAMS DURING VINYL ACETATE PRODUCTION

PRIORITY CLAIM

The present disclosure claims priority to US Patent Application Publication No. 2022/0402852 filed Apr. 27, 2022, which claims priority to International Patent Application Publication No. WO 2021/127682 filed Dec. 4, 2020, which claims priority to U.S. Provisional Patent Application No. 62/950,264 filed Dec. 19, 2019.

BACKGROUND

The present disclosure relates to methods and systems of producing vinyl acetate.

Vinyl acetate is conventionally produced via a vapor phase reaction of ethylene, oxygen, and acetic acid where the ethylene is acetoxylated. The reaction is typically conducted in a fixed bed catalyst reactor. The catalyst may comprise palladium or a palladium/gold mixture, which is supported on a silica or alumina base. In addition to the formation of vinyl acetate, the undesired combustion of ethylene to form carbon dioxide and water also takes place. Other undesired impurities that may be formed include acetaldehyde, ethyl acetate, methyl acetate, acetone, ethylene glycol diacetate, acrolein, and crotonaldehyde.

The selectivity and conversion relating to the reaction are functions of several variables including reactor temperature, component concentration, and the condition of the catalyst. Deactivation of the catalyst, which routinely occurs over time due to buildup of tars and polymeric materials on the catalyst surface and/or to structural changes of the catalyst metals, can adversely affect the reaction process, particularly with regard to selectivity. These changes in reactor performance can ultimately lead to compositional changes in the liquid stream entering the purification section of a vinyl acetate plant.

The acetoxylation of ethylene yields a crude vinyl acetate product comprising vinyl acetate, water, and carbon dioxide as well as unreacted ethylene and acetic acid, which are used in excess. The ethylene and acetic acid are recycled back to the reactor from the reaction and purification sections of the unit. Product vinyl acetate is recovered and purified in the purification section and sent to storage tanks. Wastewater is sent to a treatment facility and carbon dioxide is vented to a pollution control device. Inert gases such as nitrogen and argon may accumulate over time and may then be purged from the reaction section to minimize buildup.

Generally speaking, the rate of acetoxylation increases as the concentration of oxygen in the reactor is increased. However, the amount of oxygen that may be introduced into the reactor is limited by a flammability limit of the reaction mixture. The flammability limit is typically defined as the lowest concentration of oxygen in a mixture that will result in a pressure rise when it contacts an ignition source. If the oxygen concentration exceeds this flammability limit, a fire or explosion could result.

Various steps have been taken to minimize the risk of such a fire or explosion. For example, in the fixed-bed reactor of EP 0 845 453, the concentration of oxygen in the inlet gas composition is closely monitored and maintained at or near a threshold value. The mathematical approximations used to define this threshold value are described in EP 0 845 453, which is incorporated herein by reference. When the inlet oxygen concentration exceeds this threshold value, a shutdown signal is activated, and the reaction is quenched by shutting off the ingress of fresh oxygen into the reactor.

The conventional calculation of flammability limits and/or the establishment of non-flammability ranges, however, may be inherently inaccurate. The conventional experimental techniques and methods that are used to develop mathematical correlations generally calculate flammability limits that are low. These correlations provide a buffer from the true flammability limit. Although safety is achieved, reaction efficiencies suffer due to operation at lower oxygen concentrations than the true flammability limits would indicate.

SUMMARY OF THE INVENTION

The present disclosure relates to methods and systems of producing vinyl acetate.

According to one aspect of the present disclosure a method comprises: reacting the feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes; cooling the crude vinyl acetate stream in a heat exchanger; measuring and/or determining conditions of a pressure of the feed stream or the reactor, a temperature of the feed stream or the reactor, and a concentration of at least one component in the feed stream; measuring and/or determining an oxygen content ($[O_2]$) of the feed stream; and initiating a shutdown procedure or a remedial step when $AFL_{min} > FL - [O_2]$ is true, wherein the minimum approach to flammability limit ($AFL_{min}$) and the flammability limit (FL) formula are based on the conditions, and wherein the FL formula includes at least one interaction term.

According to one aspect of the present disclosure a method comprises: reacting the feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes; cooling the crude vinyl acetate stream in a heat exchanger; separating the crude vinyl acetate stream into a tail gas stream, a flash gas stream, and a vinyl acetate stream, wherein the tail gas stream comprises ethylene, carbon dioxide, alkanes, and oxygen, wherein the flash gas stream comprises ethylene, carbon dioxide, alkanes, and oxygen, and wherein the vinyl acetate stream comprises vinyl acetate, water, and acetic acid; heating the tail gas stream in the heat exchanger; measuring and/or determining conditions of a pressure of the tail gas stream after heating, a temperature of the tail gas stream after heating, and a concentration of at least one component in the tail gas stream after heating; measuring and/or determining an oxygen content ($[O_2]$) of the tail gas stream after heating; and initiating a shutdown procedure or a remedial step when $AFL_{min} > FL - [O_2]$ is true, wherein the minimum approach to flammability limit ($AFL_{min}$) and the flammability limit (FL) formula are based on the conditions, and wherein the FL formula includes at least one interaction term.

According to one aspect of the present disclosure a method comprises: reacting the feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes; cooling the crude vinyl acetate stream in a heat exchanger; separating the crude vinyl acetate stream into a tail gas stream, a flash gas stream, and a vinyl acetate stream, wherein the tail gas stream comprises ethylene, carbon dioxide, alkanes, and oxygen, wherein the flash gas stream comprises ethylene, carbon dioxide, alkanes, and oxygen, and wherein the vinyl acetate stream comprises vinyl acetate, water, and acetic acid; removing at least a portion of the carbon dioxide from the flash gas stream to produce a $CO_2$ removal overheads stream; measuring and/or determining conditions of a pressure of the $CO_2$ removal overheads stream, a temperature of the $CO_2$ removal overheads stream, and a concentration of at least one component in the $CO_2$ removal overheads stream; measuring and/or determining an oxygen content ($[O_2]$) of the $CO_2$ removal overheads stream; and initiating a shutdown procedure or a remedial step when $AFL_{min} > FL-[O_2]$ is true, wherein the minimum approach to flammability limit ($AFL_{min}$) and the flammability limit (FL) formula are based on the conditions, and wherein the FL formula includes at least one interaction term.

According to one aspect of the present disclosure a method comprises: reacting the feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes; cooling the crude vinyl acetate stream in a heat exchanger; separating the crude vinyl acetate stream into a tail gas stream, a flash gas stream, and a vinyl acetate stream, wherein the tail gas stream comprises ethylene, carbon dioxide, alkanes, and oxygen, wherein the flash gas stream comprises ethylene, carbon dioxide, alkanes, and oxygen, and wherein the vinyl acetate stream comprises vinyl acetate, water, and acetic acid; heating the tail gas stream in the heat exchanger; removing at least a portion of the carbon dioxide from the flash gas stream to produce a $CO_2$ removal overheads stream; mixing vaporized acetic acid with the tail gas stream after heating and the $CO_2$ removal overheads stream in a vaporizer to produce a vaporized stream; adding oxygen to the vaporized stream to produce the feed stream; measuring and/or determining conditions according to (a), (b), and/or (c): (a) a pressure of the feed stream or the reactor, a temperature of the feed stream or the reactor, and a concentration of at least one component in the feed stream; (b) a pressure of the tail gas stream after heating, a temperature of the tail gas stream after heating, and a concentration of at least one component in the tail gas stream after heating; (c) a pressure of the $CO_2$ removal overheads stream, a temperature of the $CO_2$ removal overheads stream, and a concentration of at least one component in the $CO_2$ removal overheads stream; and wherein (a) has associated therewith a first minimum approach to flammability limit ($AFL_{min}$) and a first flammability limit (FL) formula based on the conditions of (a), wherein (b) has associated therewith a second minimum $AFL_{min}$ and a second FL formula based on the conditions of (b), wherein (c) has associated therewith a third minimum $AFL_{min}$ and a third FL formula based on the conditions of (c), wherein one or more of the first FL formula, second FL formula, and the third second FL formula include at least one interaction term; measuring and/or determining an oxygen content ($[O_2]$) of a stream selected from the group consisting of: the feed stream, the tail gas stream after heating, the $CO_2$ removal overheads stream, and any combination thereof; and initiating a shutdown procedure or a remedial step when $AFL_{min} > FL-[O_2]$ is true for one or more of (a), (b), or (c).

According to one aspect of the present disclosure a method comprises: reacting the feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes; cooling the crude vinyl acetate stream in a heat exchanger; separating the crude vinyl acetate stream into a tail gas stream, a flash gas stream, and a vinyl acetate stream; conveying a portion of the flash gas stream to an ethylene recovery process having a vent stream; measuring conditions of a pressure of the vent stream, a temperature of the vent stream, and a concentration of at least one component in the vent stream, wherein the conditions have associated therewith a minimum approach to flammability limit ($AFL_{min}$) and a flammability limit (FL) formula that includes at least one interaction term; measuring an oxygen content ($[O_2]$) in the vent stream; and changing an operating condition of the ethylene recovery process when $AFL_{min} > FL-[O_2]$ is true for the vent stream to return the ethylene recovery process to $AFL_{min} \leq FL-[O_2]$.

BRIEF DESCRIPTION OF THE DRAWINGS

The following FIGURES are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

The FIGURE illustrates a process flow diagram of an example vinyl acetate production process of the present disclosure.

DETAILED DESCRIPTION

As described previously, vinyl acetate reactors are operated based on a flammability limit that achieves safety but greatly reduces reaction efficiency and consequently, increases manufacturing cost. Further, where manufacturers monitor for flammability in additional locations along the vinyl acetate production process, the same conventional calculation of flammability limits and/or the establishment of non-flammable ranges are often used even though the conditions (e.g., temperature and pressure) and components in the corresponding composition are different in different locations along the production process. Therefore, the need exists for a vinyl acetate production process that utilizes more accurate flammability limit correlations throughout the vinyl acetate production process, which provides safety control and improved operational efficiencies.

The present disclosure relates to methods and systems of producing vinyl acetate using flammability limit (FL) formulas with improved efficiencies at more than one location in the vinyl acetate production process. Herein, FLs can be used for four portions of the vinyl acetate production process: the reactor, the process-to-process heat exchangers, the carbon dioxide removal system, and the ethylene recovery system (described in further detail herein).

FLs described herein are functions of operating conditions and include at least one interaction term that represents the interrelation of two or more of the operating conditions (e.g., temperature, pressure, and component concentration) on the FL. FL is typically expressed in units of mol percent oxygen. However, one skilled in the art would recognize that other units are acceptable.

Described herein are four types of interaction terms: a component-component interaction term, a temperature-component interaction term, a pressure-component interaction term, and a pressure-temperature interaction term. Each FL formula described herein includes at least one of the interaction terms. Further, for each interaction term included, each FL described herein may include one or more of said interaction term. For example, a first FL may include one component-component interaction term, two temperature-component interaction terms, no pressure-component interaction term, and a pressure-temperature interaction term. Further, a second FL may include three component-component interaction terms, two temperature-component interaction terms, two pressure-component interaction terms, and no pressure-temperature interaction term. Preferably, at least one (and more preferably at least three) component-component interaction terms are included in FL formulas.

Equation 1a is a general formula for calculating a flammability limit described herein.

$$FL = \alpha + \beta P^a + \gamma T^b + \Sigma \delta_i [C_i]^c + \Sigma \varepsilon_j I_j \qquad \text{Equation 1}$$

where FL is flammability limit; $\alpha$, $\beta$, $\gamma$, $\delta_i$, and $\varepsilon_1$ are factors that can be determined experimentally for a given range of compositions, pressures, and temperatures; P is pressure; T is temperature; $[C_i]$ is the concentration of each of i number of C components considered in the composition; $I_j$ is the j number of interaction terms I considered; and a, b, and c are exponents (typically 1 or 2).

The number i of C components considered in the composition for Equation 1 may range from 0 to 10 or more, or from 1 to 10, or from 2 to 7. The number j of I components considered in the composition for Equation 1 may range from 1 to 20 or more, or from 1 to 15, or from 2 to 10, or from 4 to 12.

Interaction terms can be two or more operating conditions times each other (e.g., $I = P^d * [C]^e$ (d and e are exponents, typically 1) is an example pressure-component interaction term, $I = T^f * [C]^g$ (f and g are exponents, typically 1) is an example temperature-component interaction term, $I = [C_1]^h * [C_2]^k$ (h and k are exponents, typically 1) is an example component-component interaction term where the two components may be the same or different, and $I = P^l * T^m$ (l and m are exponents, typically 1) is the pressure-temperature interaction term. While illustrated herein as the conditions of the interaction term being multiplied, other mathematical relationships may be used. For example, if an inverse relationship between two components is identified, the interaction term may include a first condition divided by a second condition rather than multiplied as illustrated in the foregoing example.

FL formulas can include concentration terms for one or more of the components in the composition under consideration. Not all components in the composition under consideration need be included in the FL formula.

FL formulas can include at least one interaction term. Preferably, a FL includes at least one of each of the four interaction terms. More preferably, a FL includes (a) two or more component-component interaction terms, (b) one or more temperature-component interaction terms, (c) one or more pressure-component interaction terms, (d) the pressure-temperature interaction term, or (e) any combination of two or more of (a)-(d).

For example, Equations 2-5 are examples of FL formulas.

$$FL = \alpha + \beta P^a + \gamma T^b + \Sigma_{1 \leq i \leq 10} \delta_i [C_i]^c + \Sigma_{1 \leq j \leq 50} \varepsilon_j I_j \qquad \text{Equation 2}$$

$$FL = \alpha + \beta P^a + \gamma T^b + \Sigma_{i=1}^{2} \delta_i [C_i]^c + \varepsilon I \qquad \text{Equation 3}$$

$$FL = \alpha + \beta P^a + \gamma T^b + \Sigma_{i=1}^{5} \delta_i [C_i]^c + \Sigma_{j=1}^{7} \varepsilon_j I_j \qquad \text{Equation 4}$$

$$FL = \alpha + \beta P^a + \gamma T^b + \Sigma_{i=1}^{3} \delta_i [C_i]^c + \Sigma_{j=1}^{8} \varepsilon_j I_j \qquad \text{Equation 5}$$

Approach to the flammability limit (AFL) is defined as the difference between the flammable limit of a composition and oxygen content ($[O_2]$) in the composition as illustrated in Equation 6. AFL is typically expressed in units of mol percent oxygen in the specified gas. However, one skilled in the art would recognize that other units are acceptable and that for Equation 6 the units of FL, AFL, and $[O_2]$ should be the same.

$$AFL = FL - [O_2] \qquad \text{Equation 6}$$

At an AFL of 0, the oxygen content is equal to the flammability limit.

Each FL has a corresponding minimum AFL. The minimum AFL ($AFL_{min}$) is a threshold value that provides a value of how close one can safely operate to the FL, where safe operations are at $AFL_{min} \leq FL - [O_2]$. Methods of determining $AFL_{min}$ are known in the art and may include considerations like uncertainty in the FL formula, sensor detection limits, and sensor measurement accuracy (or error). European Patent Application No. 0 845 453 A2 describes a method for determining an approach to flammability limit and is incorporated herein by reference.

Each location in the system where FL is monitored will have a corresponding $AFL_{min}$ and FL formula (referred to herein as "$AFL_{min}$/FL combination" for short). The $AFL_{min}$/FL combinations are generally unique for different locations within the vinyl acetate production process because of the different considerations at each location. However, in some instances, two locations have the same $AFL_{min}$/FL.

The systems and methods of the present disclosure may have an $AFL_{min}$/FL combination for one or more of four portions of the vinyl acetate production process: the reactor inlet, the process-to-process heat exchanger, the carbon dioxide removal system, and the ethylene recovery system (described in further detail herein). Preferably, two or more of said portions of the vinyl acetate production process have a respective $AFL_{min}$/FL combination. More preferably, three or four of said portions of the vinyl acetate production process have a respective $AFL_{min}$/FL combination. Most preferably, all four of said portions of the vinyl acetate production process have a respective $AFL_{min}$/FL combination.

The FIGURE illustrates a process flow diagram of an example vinyl acetate production process 100 of the present disclosure. Additional components and modifications may be made to the process 100 without changing the scope of the present invention. Further, as would be recognized by one skilled in the art, the description of the process 100 and related system uses streams to describe the fluids passing through various lines. For each stream, the related system has corresponding lines (e.g., pipes or other pathways through which the corresponding fluids or other materials may pass readily) and optionally valves, pumps, compressors, heat exchangers, or other equipment to ensure proper operation of the system whether explicitly described or not.

Further, the descriptor used for individual streams does not limit the composition of said streams to consisting of said descriptor. For example, an ethylene stream does not necessarily consist of only ethylene. Rather, the ethylene stream may comprise ethylene and a diluent gas (e.g., an inert gas). Alternatively, the ethylene stream may consist of only ethylene. Alternatively, the ethylene stream may comprise ethylene, another reactant, and optionally an inert component.

In the illustrated process 100, an acetic acid stream 102 and an ethylene stream 104 are introduced to a vaporizer 106. Optionally, ethane may also be added to the vaporizer 106. In addition, one or more recycle streams 130, 158 (each described further herein) may also be introduced to the vaporizer 106. Optionally, one or more of the recycle streams 130, 158 can be combined with the acetic acid stream 102 (not shown) before introduction to the vaporizer 106.

The temperature and pressure of vaporizer 106 may vary over a wide range. The vaporizer 106 preferably operates at a temperature from 100° C. to 250° C., or from 100° C. to 200° C., or from 120° C. to 150° C. The operating pressure of the vaporizer 106 preferably is from 0.1 MPa to 2.03 MPa, or 0.25 MPa to 1.75 MPa, or 0.5 MPa to 1.5 MPa. The vaporizer 106 produces a vaporized feed stream 108. The vaporized feed stream 108 exits the vaporizer 106 and combines with an oxygen stream 110 to produce a combined feed stream 112. The combined feed stream 112 is analyzed by sensors 114 prior to being fed to a vinyl acetate reactor 116.

The sensors 114 include a water sensor for determining the concentration of water in the combined feed stream 112. The sensors 114 can optionally also include a temperature sensor, a pressure sensor, a flow rate sensor, composition sensors (e.g., gas chromatography, infrared spectroscopy, and oxygen analyzers) and the like, and any combination thereof. Each of the individual sensors can be present singularly or in a plurality. Having a plurality of a specific sensor provides redundancies that minimize downtime for sensor replacement and mitigate safety issues resulting from a failing or out of calibration sensor. While the sensors 114 are generally illustrated as upstream of the vinyl acetate reactor 116, said sensors may be placed in other locations where calculations may be performed to estimate a condition (e.g., temperature, pressure, or component concentration) at the reactor inlet or other suitable location for which a first $AFL_{min}/FL$ combination is applied.

As described herein, many locations within the process 100 contain compositions that have the potential to become flammable if not monitored and conditions adjusted as needed. Portions of the process 100 and related system should be operated to mitigate the risk of fires and explosions. One such location is the combined feed stream 112 under reaction conditions. Accordingly, the composition of the combined feed stream 112, the temperature of the combined feed stream 112 and/or of the vinyl acetate reactor 116, and the pressure of the combined feed stream 112 and/or of the vinyl acetate reactor 116 may be adjusted to provide for safe operation of the vinyl acetate reactor 116.

The operating conditions in the vinyl acetate reactor 116 may be adjusted based on the composition of the combined feed stream 112. Generally, suitable ranges for the operating conditions in the vinyl acetate reactor 116 are provided below.

Regarding the general operating conditions of the vinyl acetate reactor 116, the molar ratio of ethylene to oxygen when producing vinyl acetate is preferably less than 20:1 in the vinyl acetate reactor 116 (e.g., 1:1 to 20:1, or 1:1 to 10:1, or 1.5:1 to 5:1, or 2:1 to 4:1). Further, the molar ratio of acetic acid to oxygen is preferably less than 10:1 in the vinyl acetate reactor 116 (e.g., 0.5:1 to 10:1, 0.5:1 to 5:1, or 0.5:1 to 3:1). The molar ratio of ethylene to acetic acid is preferably less than 10:1 in the vinyl acetate reactor 116 (e.g., 1:1 to 10:1, or 1:1 to 5:1, or 2:1 to 3:1). Accordingly, the combined feed stream 112 comprise the ethylene, oxygen, and acetic acid in said molar ratios.

The vinyl acetate reactor 116 may be a shell and tube reactor that is capable, through a heat exchange medium, of absorbing heat generated by the exothermic reaction and controlling the temperature therein within a temperature range of 100° C. to 250° C., or 110° C. to 200° C., or 120° C. to 180° C. The pressure in the vinyl acetate reactor 116 may be maintained at 0.5 MPa to 2.5 MPa, or 0.5 MPa to 2 MPa.

Further, the vinyl acetate reactor 116 may be a fixed bed reactor or a fluidized bed reactor, preferably a fixed bed reactor that contains a catalyst suitable for acetoxylation of ethylene. Suitable catalysts for the production of vinyl acetate are described, for example, in U.S. Pat. Nos. 3,743,607; 3,775,342; 5,557,014; 5,990,344; 5,998,659; 6,022,823; 6,057,260; and 6,472,556, each of which is incorporated herein by reference. Suitable catalysts may comprise palladium, gold, vanadium, and mixtures thereof. Particular preference is given to the catalysts palladium acetate/potassium acetate/cadmium acetate and palladium acetate/barium acetolaurate/potassium acetate. In general, the palladium content of the catalyst is from 0.5 wt % to 5 wt %, or 0.5 wt % to 3 wt %, or 0.6 wt % to 2 wt %. When gold or one of its compounds is used, it is added in a proportion of 0.01 wt % to 4 wt %, or 0.2 wt % to 2 wt %, or 0.3 wt % to 1.5 wt %. The catalysts also preferably contain a refractory support, preferably a metal oxide such as silica, silica-alumina, titania, or zirconia, more preferably silica.

The operating conditions under which the vinyl acetate reactor 116 is operated may be based on a first $AFL_{min}/FL$ combination. The first FL may be based on the pressure of the combined feed stream 112 or in the vinyl acetate reactor 116, the temperature of the combined feed stream 112 or in the vinyl acetate reactor 116, and the concentration of individual components in the combined feed stream 112. Because the process 100 uses one or more recycle streams 130, 158, 168 and diluents can be included, the components in the combined feed stream 112 are more than ethylene, acetic acid, and oxygen. Examples of components in the combined feed stream 112 where the concentration of said components may be used (alone and/or in an interaction term) in a first FL formula (e.g., according to one of Equations 1-5) include, but are not limited to, ethylene, acetic acid, methane, ethane, propane, water, nitrogen, argon, and carbon dioxide.

The concentration of components in the various streams described herein can be measured directly or calculated based on a measurement of a different component. For example, an acetic acid content (accounting for dimerization) in a stream may be calculated based on measurements. Then, the acetic acid content may be derived from the water content. Further, measurements or values derived from measurements need not be at the location of interest. For example, the water content at the reactor inlet may be derived from the water content of a recycle stream coming from purification processes 148 (referred to in paragraph 55) but not represented on The FIGURE). Accordingly, when a condition value (e.g., temperature value, pressure value, or concentration of a component in a stream) is described herein, condition value is not limited to a direct measurement at said location but encompasses a derived value for said location based on measurements at that location or other locations in the process 100.

A discussion of FL equation derivation is provided in the Examples section. The first FL may be based on the pressure in the vinyl acetate reactor 116, the temperature of the vinyl acetate reactor 116, and the concentration of individual components in the vinyl acetate reactor 116 at the inlet. Again, generally, the first FL formula may include at least one interaction term. Preferably, the first FL formula includes at least one of each of the four interactions terms. More preferably, the first FL formula includes (a) two or more component-component interaction terms, (b) one or more temperature-component interaction terms, (c) one or more pressure-component interaction terms, (d) the pressure-temperature interaction term, or (e) any combination of two or more of (a)-(d). Components that may be included in interaction terms of the first FL formula include, but are not limited to, a concentration of ethane ($[C_2H_6]$), a concentration of methane ($[CH_4]$), a concentration of carbon dioxide ($[CO_2]$), a concentration of acetic acid ($[HAc]$), a concentration of water ($[H_2O]$), a concentration of ethylene ($[C_2H_4]$), a concentration of propane ($[C_3H_8]$), and any combination thereof. Accordingly, examples of interaction terms that may be included in the first FL formula may include, but are not limited to, $P*T$, $P*[C_2H_6]$, $P*[CH_4]$, $P*[CO_2]$, $P*[HAc]$, $P*[H_2O]$, $P*[C_2H_4]$, $P*[C_3H_8]$, $T*[C_2H_6]$, $T*[CH_4]$, $T*[CO_2]$, $T*[HAc]$, $T*[H_2O]$, $T*[C_2H_4]$, $T*[C_3H_8]$, $[C_2H_6]*[CH_4]$, $[C_2H_6]*[CO_2]$, $[C_2H_6]*[HAc]$, $[C_2H_6]*[H_2O]$, $[C_2H_6]*[C_2H_4]$, $[C_2H_6]*[C_3H_8]$, $[CH_4]*[CO_2]$, $[CH_4]*[HAc]$, $[CH_4]*[H_2O]$, $[CH_4]*[C_2H_4]$, $[CH_4]*[C_3H_8]$, $[CO_2]*[HAc]$, $[CO_2]*[H_2O]$, $[CO_2]*[C_2H_4]$, $[CO_2]*[C_3H_8]$, $[HAc]*[H_2O]$, $[HAc]*[C_2H_4]$, $[HAc]*[C_3H_8]$, $[H_2O]*[C_2H_4]$, $[H_2O]*[C_3H_8]$, $[C_2H_4]*[C_3H_8]$, and any combination thereof. Inert gases may optionally be included if the inert gas effects to the heat capacity of the gas mixture. Accordingly, examples of interaction terms that may further be included in the first FL formula may include, but are not limited to, $P*[inert]$, $T*[inert]$, $[inert]*[C_2H_6]$, $[inert]*[CH_4]$, $[inert]*[CO_2]$, $[inert]*[HAc]$, $[inert]*[H_2O]$, $[inert]*[C_2H_4]$, $[inert]*[C_3H_8]$, $[inert\ a]*[intert\ b]$, and any combination thereof. Examples of inert gases used in vinyl acetate production include, but are not limited to, argon, nitrogen, and the like, and any combination thereof. In the foregoing examples of interaction terms (both lists), the corresponding exponents described above for each component of the interaction term is 1. However, other exponents (e.g., $-2$, $-1$, $-0.5$, $0.5$, $1$, $2$, and so on) may be used.

The conditions of the vinyl acetate reactor 116 may be monitored and used to calculate the first FL and identify violations to the first minimum AFL. For example, when in operation, the first FL is continuously calculated to account for variations in the operating conditions (e.g., pressure, temperature, and concentration of individual components in the combined feed stream 112), and the oxygen content (mol percent oxygen) in the combined feed stream 112 is measured continuously to ensure operation within the minimum AFL (i.e., $AFL_{min} \leq FL-[O_2]$). If the minimum AFL is violated (i.e., the real-time AFL is less than the minimum AFL or $AFL_{min} > FL-[O_2]$), the process 100 may enter a shutdown procedure or undergo a remedial step so that the minimum AFL is not violated.

Referring again to The FIGURE, the vinyl acetate reaction in the reactor 116 produces a crude vinyl acetate stream 118. Depending on conversion and reaction conditions, the crude vinyl acetate stream 118 can comprise 5 wt % to 30 wt % vinyl acetate, 5 wt % to 40 wt % acetic acid, 0.1 wt % to 10 wt % water, 10 wt % to 80 wt % ethylene, 1 wt % to 40 wt % carbon dioxide, 0.1 wt % to 50 wt % alkanes (e.g., methane, ethane, or mixtures thereof), and 0.1 wt % to 15 wt % oxygen. Optionally, the crude vinyl acetate stream 118 may also comprise 0.01 wt % to 10 wt % ethyl acetate. The crude vinyl acetate stream 118 may comprise other compounds such as methyl acetate, acetaldehyde, acrolein, propane, and inerts such as nitrogen or argon. Generally, these other compounds, except for inerts, are present in very low amounts.

The crude vinyl acetate stream 118 passes through a heat exchanger 120 to reduce the temperature of the crude vinyl acetate stream 118 and then to a separator 122 (e.g., a distillation column). Preferably, the crude vinyl acetate stream 118 is cooled to a temperature of 80° C. to 145° C., or 90° C. to 135° C., prior to being introduced into the separator 122. Preferably, no condensation of the liquefiable components occurs and the cooled crude vinyl acetate stream 118 is introduced to the separator 122 as gas.

The energy to separate the components of the crude vinyl acetate stream 118 may be provided by the heat of reaction in the reactor 116. In some embodiments, there may be an optional reboiler dedicated to increasing the separation energy within the separator 122.

The separator 122 separates the crude vinyl acetate stream 118 into at least two streams: an overheads stream 124 and a bottoms stream 126. The overheads stream 124 can comprise ethylene, carbon dioxide, water, alkanes (e.g., methane, ethane, propane or mixtures thereof), oxygen, and vinyl acetate. The bottoms stream can comprise vinyl acetate, acetic acid, water, and potentially ethylene, carbon dioxide, and alkanes.

The overheads stream 124 is conveyed to a scrubber 128 to remove vinyl acetate in the overheads stream 124. As a result, the scrubber 128 has a tail gas stream 130 and a bottoms stream 132. Vinyl acetate scrubbing can be achieved by passing the overheads stream 124 through a mixture of water and acetic acid.

The tail gas stream 130 comprises ethylene, carbon dioxide, alkanes, and oxygen. The conditions (e.g., temperature, pressure, and/or composition of components) of the tail gas stream 130 may be measured using sensors 134. The sensors 134 may include, but are not limited to, a temperature sensor, a pressure sensor, a flow rate sensor, composition sensors (e.g., gas chromatography, infrared spectroscopy, and oxygen analyzers) and the like, and any combination thereof. Each of the individual sensors can be present singularly or in a plurality. Having a plurality of a specific sensor provides redundancies that minimize downtime for sensor replacement and mitigate safety issues resulting from a failing or out of calibration sensor. While the sensors 134 are generally illustrated as downstream of the scrubber 128 along the tail gas stream 130, said sensors may be placed in other locations where calculations may be performed to estimate a condition (e.g., temperature, pressure, or component concentration) of the tail gas stream 130 post scrubber 128.

The tail gas stream 130 (also referred to as a recycle stream) is conveyed back to the vaporizer 106 through the heat exchanger 120, where the crude vinyl acetate stream 118 heats the tail gas stream 130. Optionally, the tail gas stream 130 can be augmented with or otherwise have added thereto other streams including other recycle streams (not shown) in the process and feed streams. As illustrated, an ethylene feed steam 136 and a methane feed stream 138 (or other ballast gas stream) are combined (e.g. mixed with or entrained with) with the tail gas stream 130.

Additionally, between the scrubber 128 and the heat exchanger 120, other processes (not illustrated) may be performed on the tail gas stream 130. For example, the tail gas stream 130 may have at least a portion of the carbon dioxide removed.

The tail gas stream 130 after being heated in the heat exchanger 120 is potentially flammable and/or explosive. Therefore, a second $AFL_{min}/FL$ combination can be used in the methods and systems of the present disclosure to monitor the flammability of the tail gas stream 130 before introduction to the vaporizer.

Accordingly, between the heat exchanger 120 and the vaporizer 106, the tail gas stream 130 is analyzed by sensors 140. Examples of sensors 140 include, but are not limited to, a temperature sensor, a pressure sensor, a flow rate sensor, composition sensors (e.g., gas chromatography, infrared spectroscopy, and oxygen analyzers) and the like, and any combination thereof. Each of the individual sensors can be present singularly or in a plurality. Having a plurality of a specific sensor provides redundancies that minimize downtime for sensor replacement and mitigate safety issues resulting from a failing or out of calibration sensor. While the sensors 140 are generally illustrated as between the heat exchanger 120 and the vaporizer 106, said sensors may be placed in other locations where calculations may be performed to estimate a condition (e.g., temperature, pressure, or component concentration) between the heat exchanger 120 and the vaporizer 106 or other suitable location for which the second $AFL_{min}$/FL combination is applied.

A discussion of FL equation derivation is provided in the Examples section. The second FL may be based on the pressure in the line containing the tail gas stream 130, the temperature of the tail gas stream 130, and the concentration of individual components in the tail gas stream 130. Again, generally, the second FL formula may include at least one interaction term. Preferably, the second FL formula includes at least one of each of the four interaction terms. More preferably, the second FL formula includes (a) two or more component-component interaction terms, (b) one or more temperature-component interaction terms, (c) one or more pressure-component interaction terms, (d) the pressure-temperature interaction term, or (e) any combination of two or more of (a)-(d). Examples of components in the vinyl acetate reactor 116 where the concentration of said components may be used in the second FL formula (e.g., according to one of Equations 1-5) include, but are not limited to, ethylene, methane, ethane, propane, and carbon dioxide. Components that may be included in interaction terms of the second FL formula include, but are not limited to, a concentration of ethane ($[C_2H_6]$), a concentration of methane ($[CH_4]$), a concentration of carbon dioxide ($[CO_2]$), a concentration of ethylene ($[C_2H_4]$), a concentration of propane ($[C_3H_8]$), and any combination thereof. Accordingly, examples of interaction terms that may be included in the second FL formula may include, but are not limited to, P*T, P*$[C_2H_6]$, P*$[CH_4]$, P*$[CO_2]$, P*$[C_2H_4]$, P*$[C_3H_8]$, T*$[C_2H_6]$, T*$[CH_4]$, T*$[CO_2]$, T*$[C_2H_4]$, T*$[C_3H_8]$, $[C_2H_6]$*$[CH_4]$, $[C_2H_6]$*$[CO_2]$, $[C_2H_6]$*$[C_2H_4]$, $[C_2H_6]$*$[C_3H_8]$, $[CH_4]$*$[CO_2]$, $[CH_4]$*$[C_2H_4]$, $[CH_4]$*$[C_3H_8]$, $[CO_2]$*$[C_2H_4]$, $[CO_2]$*$[C_3H_8]$, $[C_2H_4]$*$[C_3H_8]$, and any combination thereof. Inert gases may optionally be included if the inert gas effects to the heat capacity of the gas mixture. Accordingly, examples of interaction terms that may further be included in the second FL formula may include, but are not limited to, P*[inert], T*[inert], [inert]*$[C_2H_6]$, [inert]*$[CH_4]$, [inert]*$[CO_2]$, [inert]*[HAc], [inert]*$[H_2O]$, [inert]*$[C_2H_4]$, [inert]*$[C_3H_8]$, [inert a]*[inert b], and any combination thereof. Examples of inert gases used in vinyl acetate production include, but are not limited to, argon, nitrogen, and the like, and any combination thereof. In the foregoing examples of interaction terms (both lists), the corresponding exponents described above for each component of the interaction term is 1. However, other exponents (e.g., −2, −1, −0.5, 0.5, 1, 2, and so on) may be used.

The conditions of the tail gas stream 130 may be monitored and used to calculate the second FL and identify violations to the second minimum AFL. For example, in operation, the second FL is continuously calculated to account for variations in the operating conditions (e.g., pressure, temperature, and concentration of individual components in the tail gas stream 130), and the oxygen content (mol percent oxygen) in the tail gas stream 130 is measured continuously to ensure operation within the second minimum AFL (i.e., $AFL_{min} \leq FL-[O_2]$). If the second minimum AFL is violated (i.e., the real-time AFL is less than the minimum AFL or $AFL_{min} > FL-[O_2]$), the process 100 may enter a shutdown procedure or undergo a remedial step so that the minimum AFL is not violated.

Referring again to The FIGURE, the bottoms stream 126 from the separator 122 and the bottoms stream 132 from the scrubber 128 can be combined and fed to a crude tank 142. Generally, the stream(s) coming into the crude tank 142 are depressurized to a pressure of 0.1 MPa to 0.15 MPa. In depressurizing the incoming stream, the ethylene, carbon dioxide, inert gases (e.g., nitrogen and/or argon), and acetic acid flash to produce a flash gas stream 144. The bottoms of the crude tank 142 primarily comprise vinyl acetate, water, and acetic acid with some ethyl acetate byproduct. The bottoms are transported as a vinyl acetate stream 146 to be purified by various processes 148 to produce the purified vinyl acetate product stream 150. Examples of purification processes 148 include, but are not limited to, azeotrope distillation, water stripping, distillation, phase separations, and the like, and any combination thereof. Examples of different processing methods and systems are described in U.S. Pat. Nos. 6,410,817, 8,993,796, and 9,045,413 and US Patent App. Pub. No. 2014/0066649, each of which is incorporated herein by reference.

Further, the purification processes 148 may produce additional streams that individually or in any combination can be recycled back to the vaporizer 106, the tail gas stream 130, the flash gas stream 144, and/or other streams within the process 100.

Optionally (not shown), a portion of the tail gas slip stream 130 may be combined with (e.g. mixed with or entrained with) the flash gas stream 144.

At least a portion of the carbon dioxide in the flash gas stream 144 (optionally having been combined with a portion of the tail gas slip stream 130) is removed before recycling back into the vaporizer 106. As illustrated, the flash gas stream 144 first passes through a $CO_2$ scrubber 152 and then a $CO_2$ absorber 156 to produce a $CO_2$ removal overheads stream 158. Between the $CO_2$ scrubber 152 and the $CO_2$ absorber 156, ethylene can be added to the flash gas stream 144 from ethylene stream 154.

The $CO_2$ removal overheads stream 158 is another potentially flammable or explosive composition where the oxygen content can be monitored for the processes and systems described herein. Therefore, a third $AFL_{min}$/FL combination can be used in the methods and systems of the present disclosure to monitor the flammability of the $CO_2$ removal overheads stream 158.

Accordingly, after the $CO_2$ absorber 156, the $CO_2$ removal overheads stream 158 is analyzed by sensors 160. Examples of sensors 160 include, but are not limited to, a temperature sensor, a pressure sensor, a flow rate sensor, composition sensors (e.g., gas chromatography, infrared spectroscopy, and oxygen analyzers) and the like, and any combination thereof. Each of the individual sensors can be present singularly or in a plurality. Having a plurality of a specific sensor provides redundancies that minimize downtime for sensor replacement and mitigate safety issues resulting from a failing or out of calibration sensor. While the sensors 160 are generally illustrated as downstream of the $CO_2$ absorber 156, said sensors 160 may be placed in other locations where calculations may be performed to estimate a condition (e.g., temperature, pressure, or component concentration) downstream of the $CO_2$ absorber 156 or other suitable location for which the third $AFL_{min}$/FL combination is applied.

A discussion of FL equation derivation is provided in the Examples section. The third FL may be based on the pressure in the line containing the $CO_2$ removal overheads stream 158, the temperature of the $CO_2$ removal overheads stream 158, and the concentration of individual components in the $CO_2$ removal overheads stream 158. Again, generally, the third FL formula may include at least one interaction term. Preferably, the third FL formula includes at least one of each of the four interaction terms. More preferably, the third FL formula includes (a) two or more component-component interaction terms, (b) one or more temperature-component interaction terms, (c) one or more pressure-component interaction terms, (d) the pressure-temperature interaction term, or (e) any combination of two or more of (a)-(d). Examples of components in the vinyl acetate reactor 116 where the concentration of said components may be used in the third FL formula (e.g., according to one of Equations 1-5) include, but are not limited to, ethylene, methane, ethane, propane, and carbon dioxide. Components that may be included in interaction terms of the second FL formula include, but are not limited to, a concentration of ethane ($[C_2H_6]$), a concentration of methane ($[CH_4]$), a concentration of carbon dioxide ($[CO_2]$), a concentration of ethylene ($[C_2H_4]$), a concentration of propane ($[C_3H_8]$), and any combination thereof. Accordingly, examples of interaction terms that may be included in the third FL formula may include, but are not limited to, $P*T$, $P*[C_2H_6]$, $P*[CH_4]$, $P*[CO_2]$, $P*[C_2H_4]$, $P*[C_3H_8]$, $T*[C_2H_6]$, $T*[CH_4]$, $T*[CO_2]$, $T*[C_2H_4]$, $T*[C_3H_8]$, $[C_2H_6]*[CH_4]$, $[C_2H_6]*[CO_2]$, $[C_2H_6]*[C_2H_4]$, $[C_2H_6]*[C_3H_8]$, $[CH_4]*[CO_2]$, $[CH_4]*[C_2H_4]$, $[CH_4]*[C_3H_8]$, $[CO_2]*[C_2H_4]$, $[CO_2]*[C_3H_8]$, $[C_2H_4]*[C_3H_8]$, and any combination thereof. Inert gases may optionally be included if the inert gas effects to the heat capacity of the gas mixture. Accordingly, examples of interaction terms that may further be included in the second FL formula may include, but are not limited to, $P*[inert]$, $T*[inert]$, $[inert]*[C_2H_6]$, $[inert]*[CH_4]$, $[inert]*[CO_2]$, $[inert]*[HAc]$, $[inert]*[H_2O]$, $[inert]*[C_2H_4]$, $[inert]*[C_3H_8]$, $[inert\ a]*[inert\ b]$, and any combination thereof. Examples of inert gases used in vinyl acetate production include, but are not limited to, argon, nitrogen, and the like, and any combination thereof. In the foregoing examples of interaction terms (both lists), the corresponding exponents described above for each component of the interaction term is 1. However, other exponents (e.g., −2, −1, −0.5, 0.5, 1, 2, and so on) may be used.

Because the tail gas stream 130 and the $CO_2$ removal overheads stream 158 have similar components, the second FL formula and the third FL formula may be the same. However, the second minimum AFL and the third minimum AFL may be different because different sensors may be used.

The conditions of the $CO_2$ removal overheads stream 158 may be monitored and used to calculate the third FL and identify violations to the third minimum AFL. For example, in operation, the third FL is continuously calculated to account for variations in the operating conditions (e.g., pressure, temperature, and concentration of individual components in the $CO_2$ removal overheads stream 158) and the oxygen content (mol percent oxygen) in the $CO_2$ removal overheads stream 158 is measured continuously to ensure operation within the third minimum AFL (i.e., $AFL_{min} \leq FL-[O_2]$). If the third minimum AFL is violated (i.e., the real-time AFL is less than the minimum AFL or $AFL_{min} > FL-[O_2]$), the process 100 may enter a shutdown procedure or undergo a remedial step so that the minimum AFL is not violated.

Referring again to The FIGURE, the $CO_2$ removal overheads stream 158 can then be passed through a heat exchanger 162 and fed into the vaporizer 106. Further, a slip stream 164 from the flash gas stream 144 and/or the $CO_2$ removal overheads stream 158 is used to purge inerts from the system. This slip stream 164 can be sent through an ethylene recovery process 166. The ethylene recovery process 162 produces an ethylene vent stream 168 and a recycle stream 172.

Examples of ethylene recovery processes 166 can include, but are not limited to, scrubbing systems, membrane recovery processes, and the like, and any combination thereof.

The ethylene recovery processes 166 can produce a vent stream 168 and additional stream(s) 172 that take the ethylene recovered to other processes or for recycling back into this process 100.

The vent stream 168 of the ethylene recovery processes 166 and related outputs streams are additional potentially flammable or explosive composition where the oxygen content can be monitored for the processes and systems described herein. Therefore, a fourth $AFL_{min}$/FL combination can be used in the methods and systems of the present disclosure to monitor the flammability of the ethylene vent stream 168.

Accordingly, after the ethylene recovery process 166, the ethylene vent stream 168 is analyzed by sensors 170. Examples of sensors 170 include, but are not limited to, a temperature sensor, a pressure sensor, a flow rate sensor, composition sensors (e.g., gas chromatography, infrared spectroscopy, and oxygen analyzers) and the like, and any combination thereof. Each of the individual sensors can be present singularly or in a plurality. Having a plurality of a specific sensor provides redundancies that minimize downtime for sensor replacement and mitigate safety issues resulting from a failing or out of calibration sensor. While the sensors 170 are generally illustrated along the ethylene vent stream 168, said sensors 170 may be placed in other locations where calculations may be performed to estimate a condition (e.g., temperature, pressure, or component concentration) ethylene vent stream 168 or other suitable location for which the fourth $AFL_{min}$/FL combination is applied.

A discussion of FL equation derivation is provided in the Examples section. The fourth FL may be based on the pressure in the line containing the ethylene vent stream 168, the temperature of the ethylene vent stream 168, and the concentration of individual components in the ethylene vent stream 168. Again, generally, the fourth FL formula may include at least one interaction term. Preferably, the fourth FL formula includes at least one of each of the four interaction terms. More preferably, the fourth FL formula includes (a) two or more component-component interaction terms, (b) one or more temperature-component interaction terms, (c) one or more pressure-component interaction terms, (d) the pressure-temperature interaction term, or (e) any combination of two or more of (a)-(d). Examples of components in the vinyl acetate reactor 116 where the concentration of said components may be used in the fourth FL formula (e.g., according to one of Equations 1-5) include, but are not limited to, ethylene, methane, ethane, propane, and carbon dioxide. Components that may be included in interaction terms of the second FL formula include, but are not limited to, a concentration of ethane ($[C_2H_6]$), a concentration of methane ($[CH_4]$), a concentration of carbon dioxide ($[CO_2]$), a concentration of ethylene ($[C_2H_4]$), a concentration of propane ($[C_3H_8]$), and any combination thereof. Accordingly, examples of interaction terms that may be included in the second FL formula may include, but are not limited to, P*T, P*$[C_2H_6]$, P*$[CH_4]$, P*$[CO_2]$, P*$[C_2H_4]$, P*$[C_3H_8]$, T*$[C_2H_6]$, T*$[CH_4]$, T*$[CO_2]$, T*$[C_2H_4]$, T*$[C_3H_8]$, $[C_2H_6]$*$[CH_4]$, $[C_2H_6]$*$[CO_2]$, $[C_2H_6]$*$[C_2H_4]$, $[C_2H_6]$*$[C_3H_8]$, $[CH_4]$*$[CO_2]$, $[CH_4]$*$[C_2H_4]$, $[CH_4]$*$[C_3H_8]$, $[CO_2]$*$[C_2H_4]$, $[CO_2]$*$[C_3H_8]$, $[C_2H_4]$*$[C_3H_8]$, and any combination thereof. Inert gases may optionally be included if the inert gas effects to the heat capacity of the gas mixture. Accordingly, examples of interaction terms that may further be included in the second FL formula may include, but are not limited to, P*[inert], T*[inert], [inert]*$[C_2H_6]$, [inert]*$[CH_4]$, [inert]*$[CO_2]$, [inert]*[HAc], [inert]*$[H_2O]$, [inert]*$[C_2H_4]$, [inert]*$[C_3H_8]$, [inert a]*[inert b], and any combination thereof. Examples of inert gases used in vinyl acetate production include, but are not limited to, argon, nitrogen, and the like, and any combination thereof. In the foregoing examples of interaction terms (both lists), the corresponding exponents described above for each component of the interaction term is 1. However, other exponents (e.g., −2, −1, −0.5, 0.5, 1, 2, and so on) may be used.

The conditions of ethylene recovery process 166 and/or the ethylene vent stream 168 may be monitored and used to calculate the fourth FL and identify violations to the fourth minimum AFL. For example, in operation, the fourth FL is continuously calculated to account for variations in the operating conditions (e.g., pressure, temperature, and concentration of individual components in the ethylene vent stream 164) and the oxygen content (mol percent oxygen) in the ethylene vent stream 164 is measured continuously to ensure operation within the fourth minimum AFL (i.e., $AFL_{min} \leq FL-[O_2]$). Because the ethylene recovery process 166 and/or the ethylene vent stream 168 are somewhat autonomous from the rest of the process 100, a violation of fourth minimum AFL (i.e., the real-time AFL is less than the minimum AFL or $AFL_{min}>FL-[O_2]$) may result in less severe actions than shutting down the process 100. Generally, an operating condition of the ethylene recovery process 166 is changed to return the ethylene recovery process 166 and/or the ethylene vent stream 168 to safe operation. For example, the slip stream 164 flow rate may be changed and/or a diluent gas (e.g., an inert gas like nitrogen or argon) maybe added to stream 168. Other suitable actions that can be taken to return the ethylene recovery process 166 and/or the ethylene vent stream 168 to safe operation will be apparent to those skilled in the art.

While The FIGURE illustrates the process 100 in general, one skilled in the art would recognize how to adapt the teachings of the present disclosure to other vinyl acetate production processes that may vary from the illustrated process 100. Examples of different vinyl acetate production processes and systems are described in U.S. Pat. Nos. 6,410,817, 8,993,796, and 9,045,413 and US Patent App. Pub. No. 2014/0066649, each of which is incorporated herein by reference.

EXAMPLE EMBODIMENTS

A first nonlimiting example method of the present disclosure comprises: reacting the feed stream 112 comprising acetic acid, ethylene, oxygen, carbon dioxide, alkanes, and water in a reactor 116 to produce a crude vinyl acetate stream 118 comprising vinyl acetate, acetic acid, water, ethylene, carbon dioxide, and alkanes; cooling the crude vinyl acetate stream 118 in a heat exchanger 120; measuring and/or determining conditions of a pressure of the feed stream 112 or of the reactor 116, a temperature of the feed stream 112 or of the reactor 116, and a concentration of at least one component in the feed stream 112; measuring and/or determining an oxygen content ($[O_2]$) of the feed stream 112; and initiating a shutdown procedure or a remedial step when $AFL_{min}>FL-[O_2]$ is true, wherein the minimum approach to flammability limit ($AFL_{min}$) and the flammability limit (FL) formula are based on the conditions, and wherein the FL formula includes at least one interaction term.

A second nonlimiting example method of the present disclosure comprises: reacting the feed stream 112 comprising acetic acid, ethylene, oxygen, carbon dioxide, alkanes, and water in a reactor 116 to produce a crude vinyl acetate stream 118 comprising vinyl acetate, acetic acid, water, ethylene, carbon dioxide, and alkanes; cooling the crude vinyl acetate stream 118 in a heat exchanger 120; separating the crude vinyl acetate stream 118 into a tail gas stream 130, a flash gas stream 144, and a vinyl acetate stream 146, wherein the tail gas stream 130 comprises ethylene, carbon dioxide, alkanes, and oxygen, wherein the flash gas stream 144 comprises ethylene, carbon dioxide, alkanes, and oxygen, and wherein the vinyl acetate stream 146 comprises vinyl acetate, water, and acetic acid; heating the tail gas stream 130 in the heat exchanger 120; measuring and/or determining conditions of a pressure of the tail gas stream 130 after heating, a temperature of the tail gas stream 130 after heating, and a concentration of at least one component in the tail gas stream 130 after heating; measuring and/or determining an oxygen content ($[O_2]$) of the tail gas stream 130 after heating; and initiating a shutdown procedure or a remedial step when $AFL_{min}>FL-[O_2]$ is true, wherein the minimum approach to flammability limit ($AFL_{min}$) and the flammability limit (FL) formula are based on the conditions, and wherein the FL formula includes at least one interaction term.

A third nonlimiting example method of the present disclosure comprises: reacting the feed stream 112 comprising acetic acid, ethylene, oxygen, carbon dioxide, alkanes, and water in a reactor 116 to produce a crude vinyl acetate stream 118 comprising vinyl acetate, acetic acid, water, ethylene, carbon dioxide, and alkanes; cooling the crude vinyl acetate stream 118 in a heat exchanger 120; separating the crude vinyl acetate stream 118 into a tail gas stream 130, a flash gas stream 144, and a vinyl acetate stream 146, wherein the tail gas stream 130 comprises ethylene, carbon dioxide, alkanes, and oxygen, wherein the flash gas stream 144 comprises ethylene, carbon dioxide, alkanes, and oxygen, and wherein the vinyl acetate stream 146 comprises vinyl acetate, water, and acetic acid; removing at least a portion of the carbon dioxide from the flash gas stream 144 to produce a $CO_2$ removal overheads stream 158; measuring and/or determining conditions of a pressure of the $CO_2$ removal overheads stream 158, a temperature of the $CO_2$ removal overheads stream 158, and a concentration of at least one component in the $CO_2$ removal overheads stream 158; measuring and/or determining an oxygen content ($[O_2]$) of the $CO_2$ removal overheads stream 158; and initiating a shutdown procedure or a remedial step when $AFL_{min}>FL-[O_2]$ is true, wherein the minimum approach to flammability limit ($AFL_{min}$) and the flammability limit (FL) formula are based on the conditions, and wherein the FL formula includes at least one interaction term.

Two or more of the first, second, and third example methods may be performed together. For example, the first and second example methods may be performed together. In another example, the first and third example methods may be performed together. In yet another example, the second and third example methods may be performed together. In another example, the first, second, and third example methods may be performed together. Additionally, recycling of streams and other process steps as described herein can be performed in combination with one or more of the first, second, and third example methods.

A fourth nonlimiting example method of the present disclosure comprises: reacting the feed stream 112 comprising acetic acid, ethylene, oxygen, carbon dioxide, alkanes, and water in a reactor 116 to produce a crude vinyl acetate stream 118 comprising vinyl acetate, acetic acid, water, ethylene, carbon dioxide, and alkanes; cooling the crude vinyl acetate stream 118 in a heat exchanger 120; separating the crude vinyl acetate stream 118 into a tail gas stream 130, a flash gas stream 144, and a vinyl acetate stream 146, wherein the tail gas stream 130 comprises ethylene, carbon dioxide, alkanes, and oxygen, wherein the flash gas stream 144 comprises ethylene, carbon dioxide, alkanes, and oxygen, and wherein the vinyl acetate stream 146 comprises vinyl acetate, water, and acetic acid; heating the tail gas stream 130 in the heat exchanger 120; removing at least a portion of the carbon dioxide from the flash gas stream 144 to produce a $CO_2$ removal overheads stream 158; mixing vaporized acetic acid with the tail gas stream 130 after heating and the $CO_2$ removal overheads stream 158 in a vaporizer 106 to produce a vaporized stream 108; adding oxygen to the vaporized stream 108 to produce the feed stream 112; measuring and/or determining conditions according (a), (b), and/or (c): (a) a pressure of the feed stream 112 or of the reactor 116, a temperature of the feed stream 112 or of the reactor 116, and a concentration of at least one component in the feed stream 112; (b) a pressure of the tail gas stream 130 after heating, a temperature of the tail gas stream 130 after heating, and a concentration of at least one component in the tail gas stream 130 after heating; (c) a pressure of the $CO_2$ removal overheads stream 158, a temperature of the $CO_2$ removal overheads stream 158, and a concentration of at least one component in the $CO_2$ removal overheads stream 158; and wherein (a) has associated therewith a first minimum approach to flammability limit ($AFL_{min}$) and a first flammability limit (FL) formula based on the conditions of (a), wherein (b) has associated therewith a second minimum $AFL_{min}$ and a second FL formula based on the conditions of (b), wherein (c) has associated therewith a third minimum $AFL_{min}$ and a third FL formula based on the conditions of (c), wherein one or more of the first FL formula, second FL formula, and the third second FL formula include at least one interaction term; measuring and/or determining an oxygen content ($[O_2]$) of a stream selected from the group consisting of: the feed stream 112, the tail gas stream 130 after heating, the $CO_2$ removal overheads stream 158, and any combination thereof; and initiating a shutdown procedure or a remedial step when $AFL_{min}>FL-[O_2]$ is true for one or more of (a), (b), or (c). The fourth nonlimiting example method may further include one or more of the following: Element 1: wherein the first FL formula, the second FL formula, and/or the third FL formula are according to Equation 1; Element 2: wherein the first $AFL_{min}$ is different than the second $AFL_{min}$ and/or the first $AFL_{min}$ is different than the third $AFL_{min}$ and/or the second $AFL_{min}$ is different than the third $AFL_{min}$; Element 3: wherein the first FL formula is different than the second FL formula and/or the first FL formula is different than the third FL formula and/or the second FL formula is different than the third FL formula; Element 4: wherein the at least one interaction term is selected from the group consisting of: a component-component interaction term, a temperature-component interaction term, a pressure-component interaction term, a pressure-temperature interaction term, and any combination thereof; Element 5: wherein the second first formula, the second FL formula, and/or the third FL formula include one or more terms selected from the group consisting of a constant, temperature, pressure, a concentration of a component in the corresponding composition; Element 6: wherein the first FL formula and/or the second FL formula and/or the third FL formula includes at least two component-component interaction terms; Element 7: wherein the first FL formula and/or the second FL formula and/or the third FL formula includes at least one pressure-component term, at least one temperature-component interaction term, a pressure-temperature interaction term, and at least two component-component interaction terms; Element 8: wherein the at least one interaction term is 3 to 15 interaction terms; Element 9: the method further comprising: combining a portion of the tail gas slip stream 130 with the flash gas stream 144 before removing at least a portion of the carbon dioxide from the flash gas stream 144; Element 10: wherein separating the crude vinyl acetate stream 118 comprises: separating the crude vinyl acetate stream 118 in a separator 122 into an overheads stream 124 and a first bottoms stream 126; separating the overheads stream 124 in a scrubber 128 into the tail gas stream 130 and a second bottoms stream 132; combining the first and second bottoms streams 126, 132; and separating the combined first and second bottoms streams 126, 132 in a crude tank 142. into the flash gas stream 144 and the vinyl acetate stream 146; Element 11: the method further comprising: purifying the vinyl acetate stream 146 into a purified vinyl acetate product stream 150; Element 12: the method further comprising: purifying the vinyl acetate stream 146 into a purified vinyl acetate product stream 150 and one or more additional streams; and recycling at least one of the additional streams back to the vaporizer 106, the tail gas stream 130, or the flash gas stream 144; Element 13: the method further comprising: adding ethylene and/or methane to the tail gas stream 130 upstream of the heat exchanger 120; Element 14: the method further comprising: removing at least a portion of the carbon dioxide from the tail gas stream 130 upstream of the heat exchanger 120; Element 15: the method further comprising: adding ethylene and/or acetic acid to the vaporizer 106; Element 16: the method further comprising: conveying a portion of the flash gas stream 144 to an ethylene recovery process 166 having a vent stream 168; measuring conditions of a pressure of the vent stream 168, a temperature of the vent stream 168, and a concentration of at least one component in the vent stream 168, wherein the conditions have associated therewith a fourth minimum approach to flammability limit ($AFL_{min}$) and a fourth flammability limit (FL) formula that includes at least one interaction term; measuring an oxygen content ($[O_2]$) in the vent stream 168; and changing an operating condition of the ethylene recovery process 166 when $AFL_{min}>FL-[O_2]$ is true for the vent stream 168 to return the ethylene recovery process 166 to $AFL_{min} \leq FL-[O_2]$; Element 17: Element 16 and wherein the fourth $AFL_{min}$ is different than the first $AFL_{min}$ and/or second $AFL_{min}$ and/or the third $AFL_{min}$; Element 18: Element 16 and wherein the fourth FL formula is different than the first FL formula and/or the second FL formula and/or the third FL formula; Element 19: Element 16 and wherein the at least one interaction term for the fourth FL formula is selected from the group consisting of: a component-component interaction term, a temperature-component interaction term, a pressure-component interaction term, a pressure-temperature interaction term, and any combination thereof; Element 20: Element 16 and wherein the second first formula, the second FL formula, and/or the third FL formula include one or more terms selected from the group consisting of a constant, temperature, pressure, a concentration of a component in the corresponding composition; Element 21: Element 16 and wherein the fourth FL formula includes at least two component-component interaction terms; Element 22: Element 16 and wherein the fourth FL formula includes at least one pressure-component term, at least one temperature-component interaction term, a pressure-temperature interaction term, and at least two component-component interaction terms; and Element 23: Element 16 and wherein the at least one interaction term for the fourth FL formula is 3 to 15 interaction terms. Examples of combinations include, but are not limited to, Element 1 in combination with one or more of Elements 2-22; Elements 2 and 3 in combination; Elements 4 and 5 in combination; two or more of Elements 2-8 in combination; two or more of Elements 9-15 in combination; one or more of Elements 2-8 in combination with one or more of Elements 9-15; Element 16 in combination with one or more of Elements 17-23; one or more of Elements 2-8 in combination with Element 16 and optionally in further combination with one or more of Elements 17-23; one or more of Elements 9-15 in combination with Element 16 and optionally in further combination with one or more of Elements 17-23 and optionally in further combination with one or more of Elements 2-8.

A fifth nonlimiting example method of the present disclosure comprises: reacting the feed stream 112 comprising acetic acid, ethylene, oxygen, carbon dioxide, alkanes, and water in a reactor 116 to produce a crude vinyl acetate stream 118 comprising vinyl acetate, acetic acid, water, ethylene, carbon dioxide, and alkanes; cooling the crude vinyl acetate stream 118 in a heat exchanger 120; separating the crude vinyl acetate stream 118 into a tail gas stream 130, a flash gas stream 144, and a vinyl acetate stream 146; conveying a portion of the flash gas stream 144 to an ethylene recovery process 166 having a vent stream 168; measuring conditions of a pressure of the vent stream 168, a temperature of the vent stream 168, and a concentration of at least one component in the vent stream 168, wherein the conditions have associated therewith a minimum approach to flammability limit ($AFL_{min}$) and a flammability limit (FL) formula that includes at least one interaction term; measuring an oxygen content ($[O_2]$) in the vent stream 168; and changing an operating condition of the ethylene recovery process 166 when $AFL_{min} > FL-[O_2]$ is true for the vent stream 168 to return the ethylene recovery process 166 to $AFL_{min} \leq FL-[O_2]$. The fifth nonlimiting example method may further include one or more of the following: Element 24: wherein the FL formula is according to Equation 1; Element 25: wherein the at least one interaction term is selected from the group consisting of: a component-component interaction term, a temperature-component interaction term, a pressure-component interaction term, a pressure-temperature interaction term, and any combination thereof; Element 26: wherein the FL formula includes at least two component-component interaction terms; Element 27: wherein the FL formula includes at least one pressure-component term, at least one temperature-component interaction term, a pressure-temperature interaction term, and at least two component-component interaction terms; and Element 28: wherein the at least one interaction term is 3 to 15 interaction terms.

To facilitate a better understanding of the embodiments of the present invention, the examples of preferred or representative embodiments are given throughout the description. In no way should these examples be read to limit, or to define, the scope of the invention.

EXAMPLES

The following describes a nonlimiting example of how to derive various FL formulas.

The general formula for FL is Equation 1.

$$FL = \alpha + \beta P^a + \gamma T^b + \Sigma \delta_i [C_i]^c + \Sigma \varepsilon_j I_j \qquad \text{Equation 1}$$

The values for the factors $\alpha$, $\beta$, $\gamma$, $\delta_i$, and $\varepsilon_j$ can be determined experimentally. Generally, experimental determination of such factors involves setting reasonable potential operating condition ranges for the location to which the FL formula is to be applied.

Then, under a variety of conditions within said operating condition ranges, the maximum oxygen concentration (mol percent oxygen relative to the gas as a whole) before flammability is determined experimentally. Based on the data gathered, the FL formula is derived using any data fitting models. A plurality of equations that fit the data may be obtained. Individual equations derived from data fitting models may have any number for i and j for Equation 1. The numbers for i and j and which C and I terms are in individual equations may be set by the operator before data fitting. Alternatively, the numbers for i and j and which C and I terms are in the equation may come from the data fitting model itself. A statistical analysis of the plurality of equations may be used in determining which equation to use in operation.

In a first example, the potential operating condition ranges according to Table 1 were analyzed relative to the reactor conditions and reactor inlet composition. To the extent possible, ASTM E918-09(2015) was followed to determine concentration limits of flammability for oxygen.

TABLE 1

| | |
|---|---|
| Temperature (° C.) | 135-190 |
| Pressure (psig) | 130-205 |
| Acetic acid (wt % in oxygen-free gas) | 20-40 |
| Water (wt % in oxygen-free gas) | 0-3.2 |
| Methane (mol % in oxygen-free dry gas) | 0-40 |
| Ethane (mol % in oxygen-free dry gas) | 0-40 |
| Ethylene (mol % in oxygen-free dry gas) | 35-75 |
| Carbon dioxide (mol % in oxygen-free dry gas) | 0-25 |
| Nitrogen plus argon (mol % in oxygen-free dry gas) | 2-15 |

A plurality of FL formulas were derived including Equations 7-10, where FL is flammable oxygen composition in mol % in the dry gas; P is pressure in psig; T is temperature in ° C.; $[C_2H_6]$, $[CH_4]$, and $[CO_2]$ are ethane, methane, and carbon dioxide concentrations in mol percent of the oxygen-free dry gas; [HAc] is the acetic acid concentration in weight percent in the oxygen-free gas; [H$_2$O] is water concentration in weight percent in the oxygen-free gas; dry gas is the composition of the combined feed stream 112 excluding water and acetic acid; oxygen-free dry gas is the composition of the combined feed stream 112 excluding water, acetic acid, and oxygen; and oxygen-free gas is the composition of the combined feed stream 112 excluding oxygen.

$$FL = 17.70 - 0.01487*P - 0.0260*T + 0.1960*[C_2H_6] + 0.0780*[CH_4] + 0.0805*[CO_2] - 0.265*[HAc] + 2.211*[1120] - 0.000168*T*T - 0.1467*[1120]*[1120] - 0.000127*T*[C_2H_6] - 0.000190*T*[CO_2] + 0.002369*T*[HAc] - 0.02035*T*[1120] -$$

$$FL = 10.05 - 0.0125*P - 0.0015*T + 0.2143*[C_2H_6] + 0.1482*[CH_4] + 0.0296*[CO_2] + 0.2980*[HAc] - 2.20*[H_2O] + 0.000092*P*P + 0.002608*[HAc]*[HAc] - 0.000228*T*P - 0.000203*T*[C_2H_6] - 0.001594*T*[HAc] + 0.0264*T*[H_2O] - 0.000183*P*[C_2H_6] + 0.000469*[C_2H_6]*[CO_2] + 0.000920*[C_2H_6]*[HAc] - 0.0422*[C_2H_6]*[H_2O] - 0.0594*[CH_4]*[H_2O] + 0.001639*[CO_2]*[HAc]$$

Equation 7:
$$0.000327*P*[C_2H_6] - 0.000139*P*[CH_4] + 0.00198*[C_2H_6]*[H_2O] + 0.001097*[CO_2]*[HAc] + 0.0609*[HAc]*[1120]$$

Equation 8:

$$FL = 18.22 - 0.01909*P - 0.04743*T + 0.15050*[C_2H_6] + 0.0505*[CH_4] - 0.1063*[CO_2] + 0.0666*[HAc] - 0.311*[H_2O] + 0.000186*T*[CH_4] + 0.00318*T*[H_2O] - 0.000157*P*[C_2H_6] - 0.000827*[CH_4]*[HAc] + 0.00849*[CO_2]*[HAc]$$

Equation 9:

$$FL = 19.59 - 0.01226*P - 0.0516*T - 0.210*[C_2H_6] + 0.06460*[CH_4] - 0.0389*[CO_2] + 0.0643*[HAc] + 0.423*[H_2O] + 0.003292*[HAc]*[HAc] - 0.000109*T*P + 0.00223*T*[C_2H_6] + 0.000573*T*[CO_2] - 0.000698*T*[HAc] + 0.000407*P*[HAc] - 0.0184*[C_2H_6]*[H_2O] + 0.001654*[CO_2]*[HAc]$$

Equation 10:

Statistical analysis can be used in determining which of the FL formulas (e.g., Equations 7-10 or others) to use in operation. Again, the Equations 7-10 provided herein were derived from data produced from conditions within Table 1 and are specific to the vinyl acetate system/process configurations and conditions specified in corresponding the experimental design. One skilled in the art would recognize that Equations 7-10 cannot necessarily be used in any vinyl acetate process/system. Further, one skilled in the art with the benefit of this disclosure will recognize how to, without undo experimentation, measure flammability data points within condition ranges that are appropriate for different reactors and how to take into consideration vinyl acetate system/process configurations.

In a second example, the potential operating condition ranges according to Table 2 were analyzed, which may be applicable to the process-to-process heat exchanger and/or the carbon dioxide removal system. To the extent possible, ASTM E918-09(2015) was followed to determine concentration limits of flammability for oxygen.

TABLE 2

| | |
|---|---|
| Temperature (° C.) | 80-190 |
| Pressure (psig) | 145-225 |
| Methane (mol % in oxygen-free dry gas) | 0-45 |
| Ethane (mol % in oxygen-free dry gas) | 0-45 |
| Ethylene (mol % in oxygen-free dry gas) | 35-75 |
| Carbon dioxide (mol % in oxygen-free dry gas) | 0-30 |
| Nitrogen plus argon (mol % in oxygen-free dry gas) | 0-30 |

A plurality of FL formulas were derived including Equations 11-14, where FL is flammable oxygen composition in mol % in the dry gas; P is pressure in psig; T is temperature in ° C.; $[C_2H_6]$, $[CH_4]$, and $[CO_2]$ are ethane, methane, and carbon dioxide concentrations in mol percent of the oxygen-free dry gas; and oxygen-free dry gas is the composition of the stream excluding water, acetic acid, and oxygen.

$$FL = 16.56 - 0.0622*P + 0.00560*T + 0.12947*[C_2H_6] - 0.0179*[CH_4] - 0.0242*[CO_2] - 0.000080*T*T + 0.000123*P*P + 0.000736*[CH_4]*[CH_4] - 0.000154*T*[C_2H_6] - 0.000123*T*[CH_4] - 0.000260*T*[CO_2] 0.000255*P*[C_2 1-16] + 0.000212*P*[CO_2] + 0.001656*[C_2H_6]*[CH_4] + 0.001724*[C_2H_6]*[CO_2] + 0.002705*[CH_4]*[CO_2]$$

Equation 11:

$$FL = 20.89 - 0.1031*P - 0.04083*T + 0.1723*[C_2H_6] + 0.08815*[CH_4] + 0.05032*[CO_2] + 0.000051*T*T + 0.000226*P*P - 0.000591*[C_2H_6]*[C_2H_6] + 0.000054*T*P - 0.000221*P*[C_2H_6] - 0.000121*P*[CH_4] 0.001156*[C_2H_6]*[CH_4] - 0.000482*[CH_4]*[CO_2]$$

Equation 12:

$$FL = 7.71 + 0.0486*P - 0.03223*T + 0.1447*[C_2H_6] + 0.0060*[CH_4] + 0.0466*[CO_2] + 0.000058*T*T - 0.000172*P*P + 0.000336*[C_2H_6]*[C_2H_6] + 0.000637*[CO_2]*[CO_2] - 0.000188*T*[C_2H_6] - 0.000257*P*[C_2H_6] + 0.000127*P*[CH_4] - 0.000151*P*[CO_2] + 0.000668*[C_2H_6]*[CH_4] + 0.000366*[C_2H_6]*[CO_2] + 0.001649*[CH_4]*[CO_2]$$

Equation 13:

$$FL = 12.10 + 0.0098*P - 0.02468*T + 0.0964*[C_2H_6] - 0.0323*[CH_4] + 0.00221*[CO_2] - 0.000082*P*P + 0.001022*[CH_4]*[CH_4] + 0.000023*T*P - 0.000150*T*[C_2H_6] + 0.000052*T*[CH_4] - 0.000171*P*[C_2H_6] + 0.002150*[C_2H_6]*[CH_4] + 0.001784*[C_2H_6]*[CO_2] + 0.001472*[CH_4]*[CO_2]$$

Equation 14:

Statistical analysis can be used in determining which of the FL formulas (e.g., Equations 11-14 or others) to use in operation. Again, the Equations 11-14 provided herein were derived from data produced from conditions within Table 2 and are specific to the vinyl acetate system/process configurations and conditions specified in corresponding the experimental design. One skilled in the art would recognize that Equations 11-14 cannot necessarily be used in any vinyl acetate process/system. Further, one skilled in the art with the benefit of this disclosure will recognize how to, without undo experimentation, measure flammability data points within condition ranges that are appropriate for different reactors and how to take into consideration vinyl acetate system/process configurations.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A vinyl acetate production process comprising:
   reacting a feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes;
   cooling the crude vinyl acetate stream in a heat exchanger;
   separating the crude vinyl acetate stream into a tail gas stream, a flash gas stream and a vinyl acetate stream, wherein the tail gas stream comprises ethylene, carbon dioxide, alkanes, and oxygen, wherein the flash gas stream comprises ethylene, carbon dioxide, alkanes, and oxygen, and wherein the vinyl acetate stream comprises vinyl acetate, water, and acetic acid;
   heating the tail gas stream in the heat exchanger;
   removing at least a portion of the carbon dioxide from the flash gas stream to produce a $CO_2$ removal overheads stream;
   mixing vaporized acetic acid with the tail gas stream after heating and the $CO_2$ removal overheads stream in a vaporizer to produce a vaporized stream;
   adding oxygen to the vaporized stream to produce the feed stream;
   continuously measuring and/or determining conditions in at least one location along the vinyl acetate production process, the conditions including one or more of: pressure, a temperature, and a concentration of at least one component, wherein the at least one location has associated therewith a minimum approach to flammability limit ($AFL_{min}$) and a flammability limit (FL) formula based on the conditions at the at least one location, wherein the FL formula includes at least one interaction term that represents an interrelation of two or more of the conditions;
   continuously measuring and/or determining an oxygen content ($[O_2]$) in the at least one location; and
   adjusting the conditions in the at least one location to maintain $AFL_{min} \leq FL-[O_2]$ at each of the at least one locations.

2. The vinyl acetate production process of claim 1, wherein the FL formula includes one or more interaction terms selected from the group consisting of a constant, temperature, pressure, and a concentration of a component in a corresponding composition to the FL formula.

3. The vinyl acetate production process of claim 1, wherein the FL formula includes at least two component-component interaction terms that each represent the interrelation of a concentration of two components for a corresponding composition to the FL formula.

4. The vinyl acetate production process of claim 1, wherein the at least one interaction term is selected from the group consisting of: a component-component interaction term that represents the interrelation of a concentration of two components for a corresponding composition to the FL formula, a temperature-component interaction term that represents the interrelation of temperature and a concentration of a component for the corresponding composition, a pressure-component interaction term that represents the interrelation of pressure and a concentration of a component for the corresponding composition, a pressure-temperature interaction term that represents the interrelation of pressure and temperature, and any combination thereof.

5. The vinyl acetate production process of claim 1, wherein the FL formula includes at least one pressure-component interaction term that represents the interrelation of pressure and a concentration of a component for a corresponding composition to the FL formula, at least one temperature-component interaction term that represents the interrelation of temperature and a concentration of a component for the corresponding composition, a pressure-temperature interaction term that represents the interrelation of temperature and pressure for the corresponding composition, and at least two component-component interaction terms that represents the interrelation of a concentration of two components for the corresponding composition.

6. The vinyl acetate production process of claim 1, wherein the at least one interaction term is 3 to 15 interaction terms.

7. The vinyl acetate production process of claim 1, wherein the at least one location includes along the feed stream and/or at the reactor.

8. The vinyl acetate production process of claim 1, wherein the at least one location includes along the tail gas stream between the heat exchanger and the vaporizer.

9. The vinyl acetate production process of claim 1 further comprising: combining a portion of a tail gas slip stream with the flash gas stream before removing at least a portion of the carbon dioxide from the flash gas stream.

10. The vinyl acetate production process of claim 1, wherein separating the crude vinyl acetate stream comprises:
   separating the crude vinyl acetate stream in a separator into an overheads stream and a first bottoms stream;
   separating the overheads stream in a scrubber, into the tail gas stream and a second bottoms stream;
   combining the first and second bottoms streams; and
   separating the combined first and second bottoms streams in a crude tank into the flash gas stream and the vinyl acetate stream.

11. The vinyl acetate production process of claim 1 further comprising: purifying the vinyl acetate stream into a purified vinyl acetate product stream.

12. The vinyl acetate production process of claim 1 further comprising:
purifying the vinyl acetate stream into a purified vinyl acetate product stream and one or more additional streams; and
recycling at least one of the additional streams back to the vaporizer, the tail gas stream, and/or the flash gas stream.

13. The vinyl acetate production process of claim 1 further comprising:
adding ethylene and/or methane to the tail gas stream upstream of the heat exchanger.

14. The vinyl acetate production process of claim 1 further comprising:
removing at least a portion of the carbon dioxide from the tail gas stream upstream of the heat exchanger.

15. The vinyl acetate production process of claim 1 further comprising:
adding ethylene and/or acetic acid to the vaporizer.

16. The vinyl acetate production process of claim 1 further comprising:
conveying a portion of the flash gas stream to an ethylene recovery process having a vent stream, wherein the at least one location includes along the vent stream.

17. A vinyl acetate production process comprising:
reacting a feed stream comprising acetic acid, ethylene, oxygen, carbon dioxide, alkanes, and water in a reactor to produce a crude vinyl acetate stream comprising vinyl acetate, acetic acid, water, ethylene, carbon dioxide, and alkanes;
cooling the crude vinyl acetate stream in a heat exchanger;
measuring and/or determining conditions of a pressure of the feed stream or of the reactor, a temperature of the feed stream or of the reactor, and a concentration of at least one component in the feed stream;
measuring and/or determining an oxygen content ($[O_2]$) of the feed stream; and
(i) initiating a shutdown procedure or a remedial step when $AFL_{min} > FL - [O_2]$ is true and/or (ii) adjusting the conditions to maintain $AFL_{min} \leq FL - [O_2]$, wherein the $AFL_{min}$ is a minimum approach to flammability limit and the FL is a flammability limit formula, wherein the $AFL_{min}$ and the FL are based on the conditions, and wherein the FL includes at least one interaction term that represents an interrelation of two or more operating conditions.

18. The vinyl acetate production process of claim 17, wherein the FL formula includes one or more terms selected from the group consisting of a constant, temperature, pressure, and a concentration of a component in the corresponding composition.

19. The vinyl acetate production process of claim 17, wherein the at least one interaction term is 3 to 15 interaction terms.

20. A system for producing vinyl acetate, the system comprising:
a vinyl acetate reactor configured to receive a feed stream line and to produce a crude vinyl acetate stream line;
a heat exchanger configured to receive the crude vinyl acetate stream line;
a separator configured to receive the crude vinyl acetate stream line downstream of the heat exchanger and to produce at least two stream lines comprising an overheads stream line and a first bottoms stream line;
a plurality of sensors comprising an oxygen sensor and one or more of: a temperature sensor, a pressure sensor, a flow rate sensor, and a composition sensor, wherein the plurality of sensors are at a location along the system, wherein the oxygen sensor is configured to measure or determine an oxygen content ($[O_2]$); and
a subsystem configured to (i) determine a flammability limit (FL) based on a FL formula and measurements from the plurality of sensors and (ii) determine if $AFL_{min} \leq FL - [O_2]$, wherein $AFL_{min}$ is a minimum approach to flammability limit, and wherein the FL formula includes at least one interaction term that represents an interrelation of two or more operating conditions measured by the plurality of sensors.

* * * * *